United States Patent
Askem et al.

(10) Patent No.: US 11,896,465 B2
(45) Date of Patent: *Feb. 13, 2024

(54) NEGATIVE PRESSURE WOUND THERAPY DEVICE ACTIVATION AND CONTROL

(71) Applicant: Smith & Nephew PLC, Watford (GB)

(72) Inventors: Ben Alan Askem, Leeds (GB); Victoria Beadle, Hull (GB); John Philip Gowans, Hessle (GB); Mark Hesketh, Royston (GB); Allan Kenneth Frazer Grugeon Hunt, Beverley (GB); William Kelbie, Inverness (GB); Damyn Musgrave, Cottenham (GB); Joseph William Robinson, Papworth Everard (GB)

(73) Assignee: Smith & Nephew PLC, Watford (GB)

( * ) Notice: Subject to any disclaimer, the term of this patent is extended or adjusted under 35 U.S.C. 154(b) by 398 days.

This patent is subject to a terminal disclaimer.

(21) Appl. No.: 17/406,564

(22) Filed: Aug. 19, 2021

(65) Prior Publication Data
US 2021/0378871 A1  Dec. 9, 2021

Related U.S. Application Data

(63) Continuation of application No. 16/098,625, filed as application No. PCT/EP2017/060464 on May 3, 2017, now Pat. No. 11,096,831.
(Continued)

(51) Int. Cl.
*A61M 35/00* (2006.01)
*A61M 1/00* (2006.01)
(Continued)

(52) U.S. Cl.
CPC .. *A61F 13/00068* (2013.01); *A61F 13/00063* (2013.01); *A61F 13/0216* (2013.01);
(Continued)

(58) Field of Classification Search
CPC .......... A61M 35/00; A61M 1/00; A61M 1/74; A61M 1/962; A61M 1/982;
(Continued)

(56) References Cited

U.S. PATENT DOCUMENTS 3,874,387 A   4/1975  Barbieri
4,224,941 A   9/1980  Stivala
(Continued)

FOREIGN PATENT DOCUMENTS

CN   201664463 U   12/2010
DE   19844355 A1   4/2000
(Continued)

OTHER PUBLICATIONS

International Preliminary Report on Patentability for Application No. PCT/EP2017/060464, dated Nov. 15, 2018, 9 pages.
(Continued)

*Primary Examiner* — Catharine L Anderson
*Assistant Examiner* — Ilya Y Treyger
(74) *Attorney, Agent, or Firm* — Knobbe, Martens, Olson & Bear, LLP

(57) ABSTRACT

Embodiments of negative pressure wound therapy systems and methods are disclosed. In one embodiment, an apparatus includes a wound dressing, negative pressure source, user interface, sensor, and control circuitry. The user interface can receive an activation input. The sensor can detect whether the wound dressing is positioned over a wound. The control circuitry can cause supply of negative pressure in response to receipt of the activation input and a determination that the sensor detects that the wound dressing is positioned over the wound. In addition, the control circuitry can prevent supply of negative pressure in response to a determination that the sensor does not detect that the wound dressing is positioned over the wound.

20 Claims, 5 Drawing Sheets

Related U.S. Application Data

(60) Provisional application No. 62/479,615, filed on Mar. 31, 2017, provisional application No. 62/331,056, filed on May 3, 2016.

(51) Int. Cl.
  *A61F 13/00* (2006.01)
  *A61F 13/02* (2006.01)
  *A61F 7/00* (2006.01)

(52) U.S. Cl.
  CPC .............. *A61M 1/74* (2021.05); *A61M 1/962* (2021.05); *A61M 1/982* (2021.05); *A61M 2205/13* (2013.01); *A61M 2205/502* (2013.01)

(58) Field of Classification Search
  CPC ........ A61M 2205/13; A61M 2205/502; A61M 1/964; A61M 1/96; A61F 13/00; A61F 13/02; A61F 7/00; A61F 13/00068; A61F 13/00063; A61F 13/0216
  See application file for complete search history.

(56) References Cited

U.S. PATENT DOCUMENTS

| | | |
|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,128,735 B2 | 10/2006 | Weston |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| D625,422 S | 10/2010 | Arbesman et al. |
| 7,815,616 B2 | 10/2010 | Boehringer et al. |
| 7,837,673 B2 | 11/2010 | Vogel |
| 7,846,141 B2 | 12/2010 | Weston |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,080,702 B2 | 12/2011 | Blott et al. |
| 8,092,441 B2 | 1/2012 | Sugito |
| 8,158,844 B2 | 4/2012 | McNeil |
| 8,167,869 B2 | 5/2012 | Wudyka |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,641,691 B2 | 2/2014 | Fink et al. |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,870,837 B2 | 10/2014 | Locke et al. |
| 8,905,985 B2 | 12/2014 | Allen et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,265,665 B2 | 2/2016 | Robinson et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,560,975 B2 | 2/2017 | Mei et al. |
| D787,690 S | 5/2017 | MacKay et al. |
| 9,737,649 B2 | 8/2017 | Begin et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |

(56) References Cited

U.S. PATENT DOCUMENTS

| | | |
|---|---|---|
| RE46,778 E | 4/2018 | Peron |
| 9,956,120 B2 | 5/2018 | Locke |
| 10,004,914 B2 | 6/2018 | Nettesheim et al. |
| 10,016,543 B2 | 7/2018 | Pratt et al. |
| 10,016,544 B2 | 7/2018 | Coulthard et al. |
| 10,046,095 B1 | 8/2018 | Middaugh et al. |
| 10,046,096 B2 | 8/2018 | Askem et al. |
| 10,086,117 B2 | 10/2018 | Locke et al. |
| 10,485,906 B2 | 11/2019 | Freedman et al. |
| 11,096,831 B2 * | 8/2021 | Askem .................. A61M 1/982 |
| 2003/0212357 A1 | 11/2003 | Pace |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265586 A1 | 11/2007 | Joshi et al. |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0092927 A1 | 4/2011 | Wilkes et al. |
| 2011/0112492 A1 | 5/2011 | Bharti et al. |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0215638 A1 | 8/2013 | Dabov et al. |
| 2013/0276144 A1 | 10/2013 | Hansen |
| 2014/0100536 A1 | 4/2014 | Angel |
| 2014/0343518 A1 | 11/2014 | Riesinger |
| 2015/0057625 A1 | 2/2015 | Coulthard |
| 2015/0202354 A1 | 7/2015 | Wall |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0242964 A1 | 8/2016 | Rapp et al. |
| 2016/0271305 A1 | 9/2016 | Kurihara et al. |
| 2016/0296680 A1 | 10/2016 | Simmons et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0326277 A1 | 11/2017 | Huang |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0296397 A1 | 10/2018 | Askem et al. |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0142644 A1 | 5/2019 | Askem et al. |
| 2019/0143007 A1 | 5/2019 | Askem et al. |
| 2019/0159938 A1 | 5/2019 | Askem et al. |
| 2019/0192350 A1 | 6/2019 | Gowans et al. |
| 2019/0282737 A1 | 9/2019 | Beadle et al. |
| 2020/0022846 A1 | 1/2020 | Beadle et al. |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2326295 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |

(56) References Cited

FOREIGN PATENT DOCUMENTS

| | | |
|---|---|---|
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 2249761 B1 | 4/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2781208 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 2687241 B2 | 11/2018 |
| EP | 2687243 B2 | 11/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| JP | H04354722 A | 12/1992 |
| RU | 131622 U1 | 8/2013 |
| WO | WO-2007030601 A2 | 3/2007 |
| WO | WO-2009098696 A2 | 8/2009 |
| WO | WO-2009120951 A2 | 10/2009 |
| WO | WO-2011130570 A1 | 10/2011 |
| WO | WO-2011135285 A1 | 11/2011 |
| WO | WO-2011144888 A1 | 11/2011 |
| WO | WO-2014099709 A1 | 6/2014 |
| WO | WO-2016126560 A1 | 8/2016 |
| WO | WO-2017079174 A1 | 5/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO-2018158250 A1 | 9/2018 |
| WO | WO-2018162613 A1 | 9/2018 |
| WO | WO-2018164803 A1 | 9/2018 |
| WO | WO-2018185138 A1 | 10/2018 |
| WO | WO-2018192978 A1 | 10/2018 |

OTHER PUBLICATIONS

International Search Report and Written Opinion for Application No. PCT/EP2017/060464, dated Jul. 4, 2017, 12 pages.

* cited by examiner

NEGATIVE PRESSURE WOUND THERAPY DEVICE ACTIVATION AND CONTROL

CROSS-REFERENCE TO RELATED APPLICATIONS

This application is a continuation of U.S. patent application Ser. No. 16/098,625, filed Nov. 2, 2018, which is a U.S. national stage application of International Patent Application No. PCT/EP2017/060464, filed May 3, 2017, which claims the benefit of U.S. Provisional Application No. 62/331,056, filed May 3, 2016, and U.S. Provisional Application No. 62/479,615, filed Mar. 31, 2017; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure is disclosed. The apparatus can include a wound dressing, a negative pressure source, a user interface, a first sensor, and control circuitry. The wound dressing can be placed over a wound of a patient. The negative pressure source can be disposed on or within the wound dressing, and the negative pressure source can provide negative pressure to the wound dressing via a fluid flow path. The user interface can receive an activation input. The first sensor can be integrated with the wound dressing, and the first sensor can detect whether the wound dressing is positioned over the wound. The control circuitry can be electrically coupled to the user interface and the first sensor, and the control circuitry can: cause supply of negative pressure with the negative pressure source in response to receipt of the activation input by the user interface and a determination that the first sensor detects that the wound dressing is positioned over the wound, and prevent supply of negative pressure with the negative pressure source in response to a determination that the first sensor does not detect that the wound dressing is positioned over the wound.

The apparatus of the preceding paragraph can include one or more of the following features: The control circuitry can further: start a timer in response to receipt of the activation input by the user interface and the determination that the first sensor detects that the wound dressing is positioned over the wound; and prevent supply of negative pressure with the negative pressure source in response to expiration of the timer. The control circuitry can further not start the timer in response to the determination that the first sensor does not detect that the wound dressing is positioned over the wound. The timer can expire after between 5 days and 20 days. The apparatus can further include a power source configured to supply power to one or more of the negative pressure source or the control circuitry, and the control circuitry can further increase an amount of power supplied by the power source in response to expiration of the timer. The control circuitry can prevent supply of negative pressure with the negative pressure source by one or more of: deactivation of operation of the negative pressure source, opening of a vent positioned in the fluid flow path, and closing of a valve positioned in the fluid flow path. The control circuitry can: supply negative pressure with the negative pressure source in response to receipt of the activation input by the user interface and the determination that the first sensor detects that the wound dressing is positioned over the wound for a first period of time, and prevent supply of negative pressure with the negative pressure source in response to the determination that the first sensor detects that the wound dressing is positioned over the wound for less than the first period of time. The first sensor can include one or more of a capacitive sensor, an impedance sensor, an optical sensor, a piezoresistive sensor, a piezoelectric sensor, an elastoresistive sensor, or an electrochemical sensor. The activation input can be indicative of an element of the user interface being depressed for a second period of time. The second period of time can be between 0.5 seconds and 5 seconds. The user interface can receive a deactivation input, and in response to receipt of the deactivation input by the user interface while the negative pressure source supplies negative pressure, the control circuitry can prevent supply of negative pressure with the negative pressure source. The deactivation input can be indicative of an element of the user interface being depressed for a second period of time, and the activation input is indicative of the element of the user interface being depressed for a third period of time. The second period of time and the third period of time can each be between 0.5 seconds and 5 seconds. The control circuitry can determine if the first sensor detects that the wound dressing is positioned over the wound in response to receipt of the activation input by the user interface. The apparatus can further include: a second sensor configured to monitor pressure in the fluid flow path, and a third sensor configured to monitor pressure outside the wound dressing, and wherein the control circuitry can further control supply of negative pressure with the negative pressure source according at least to a comparison of the pressure monitored by the second sensor and the pressure monitored by the third sensor. The control circuitry can further: determine a magnitude of a difference between the pressure monitored by the second sensor and the pressure monitored by the third sensor; prevent supply of negative pressure with the negative pressure source in response to a determination that the magnitude satisfies a deactivation threshold; and supply negative pressure with the negative pressure source in response to a determination that the magnitude satisfies an activation threshold, the deactivation threshold being different from the activation threshold. The control circuitry can further: sample the pressure monitored by the second sensor and the pressure monitored by the third sensor; and vary a sampling rate at which the pressure monitored by the second sensor and the pressure monitored by the third sensor are sampled. The control circuitry can vary the sampling rate according to one or more of (i) an amount of energy stored in a power source used to power the negative pressure source or the control circuitry or (ii) whether the negative pressure source is supplying negative pressure. The control circuitry can further enter a sleep mode, and the control circuitry can vary the sampling rate by entering the sleep mode. The control circuitry can further enter a sleep mode in which the control circuitry does not sample the pressure monitored by the second sensor and the pressure monitored by the third sensor until the control circuitry leaves the sleep mode. The control circuitry can further awaken from the sleep mode in response to receipt of a hardware interrupt or a software interrupt. The control circuitry can enter a sleep mode in response to the determination that the first sensor does not detect that the wound dressing is positioned over the wound. The control circuitry can enter a sleep mode while the negative pressure source supplies negative pressure. The control circuitry can further receive the user input from the user interface as a hardware interrupt.

A method of operating, using, or manufacturing the apparatus of the preceding two paragraphs is also disclosed.

In some embodiments, a method of operating a negative pressure wound therapy apparatus is disclosed. The negative pressure wound therapy apparatus can include a wound dressing, a negative pressure source disposed on or within the wound dressing, a user interface, and a first sensor integrated with the wound dressing. The method can include: receiving an activation input with the user interface; determining whether the first sensor detects that the wound dressing is positioned over a wound; in response to receiving the activation input and determining that the first sensor detects that the wound dressing is positioned over the wound, supplying negative pressure with the negative pressure source to the wound dressing via a fluid flow path; and in response to determining that the first sensor does not detect that the wound dressing is positioned over the wound, preventing supply of negative pressure with the negative pressure source to the wound dressing.

The method of the preceding paragraph can include one or more of the following features: The method can further include: starting a timer in response to receiving the activation input with the user interface and determining that the first sensor detects that the wound dressing is positioned over the wound; and preventing supply of negative pressure with the negative pressure source to the wound dressing in response to expiration of the timer. The activation input can be indicative of an element of the user interface being depressed for a second period of time. The second period of time can be between 0.5 seconds and 5 seconds. The determining whether the first sensor detects that the wound dressing can be performed in response to receiving the activation input with the user interface. The supplying negative pressure with the negative pressure source can be controlled according at least to a comparison of a pressure monitored by a second sensor and a pressure monitored by a third sensor, the second sensor monitoring the pressure in the fluid flow path, the third sensor monitoring the pressure outside the wound dressing. The method can further include: sampling a pressure monitored by a second sensor and a pressure monitored by a third sensor, the second sensor monitoring the pressure in the fluid flow path, the third sensor monitoring the pressure outside the wound dressing; and varying a sampling rate at which the pressure monitored by the second sensor and the pressure monitored by the third sensor are sampled according to one or more of: (i) an amount of energy stored in a power source used to power the negative pressure source or the control circuitry and (ii) whether the negative pressure source is supplying negative pressure.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 1:
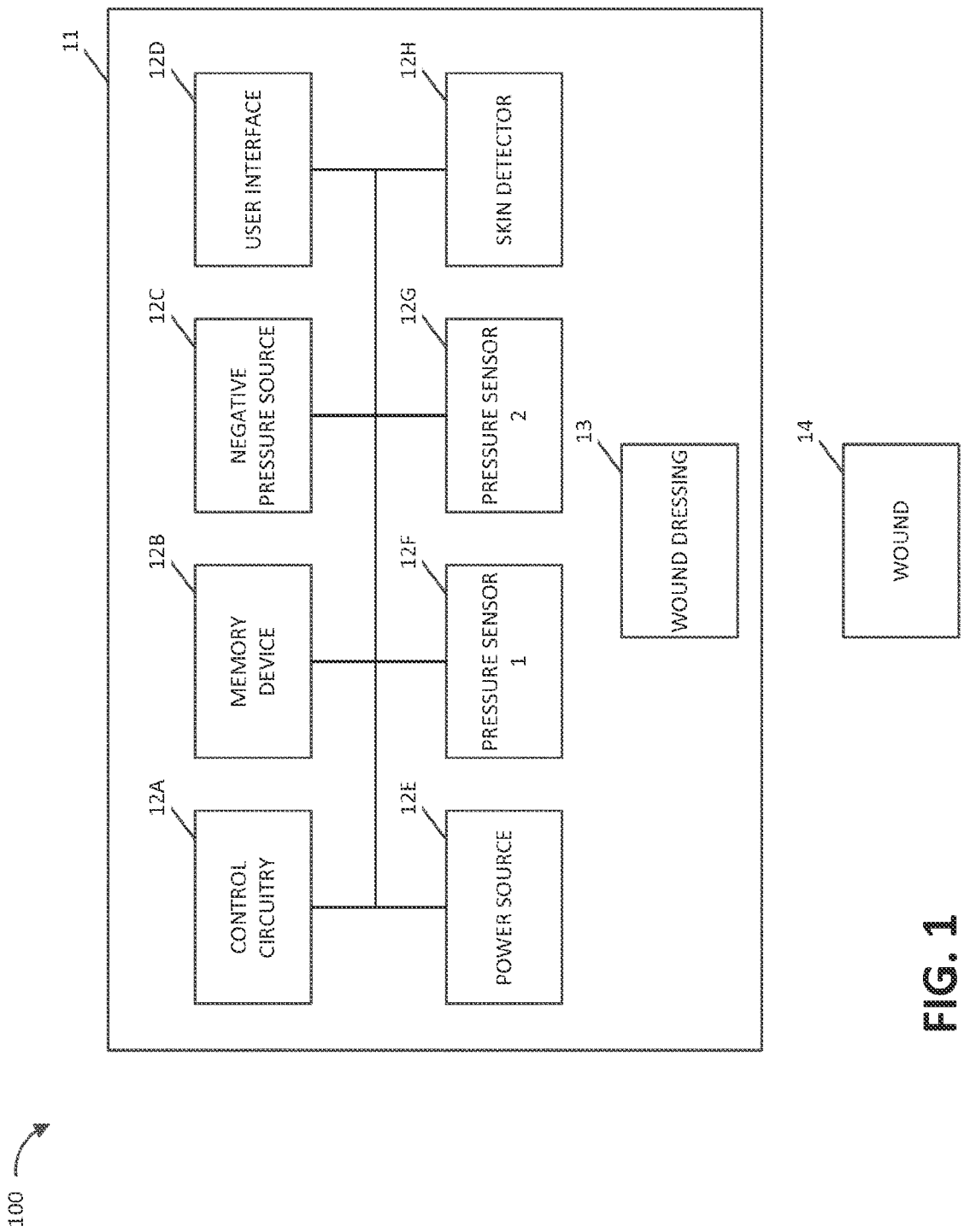
FIG. 1 illustrates a negative pressure therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Overview

Control circuitry of a TNP apparatus can delay activation of negative pressure or other functions of the TNP apparatus until after the TNP apparatus confirms contact with skin of a patient. In one example, a TNP apparatus can include a wound dressing with an integrated sensor configured to detect whether the wound dressing is in contact with skin of a patient. The TNP apparatus may not provide negative pressure to the wound dressing until the wound dressing is detected to be in contact with skin. Moreover, the TNP apparatus can provide negative pressure to the wound dressing in response to detecting that the wound dressing is in contact with skin. Additionally or alternatively, the TNP apparatus can delay activation of an end-of-life timer for the TNP apparatus until contact with skin of a patient is detected.

A TNP apparatus can determine pressure underneath a wound dressing relative to pressure external to the wound dressing. The TNP apparatus can, for instance, monitor pressure underneath the wound dressing using a first pressure sensor and monitor pressure external to the wound dressing using a second pressure sensor. The TNP apparatus can, in turn, control a negative pressure source of the TNP apparatus to attempt to achieve a desired pressure differential between the pressure underneath the wound dressing and the pressure external to the wound dressing. Control circuitry of the TNP apparatus can, in some instances, vary the sampling rate at which the pressures monitored by the first and second pressure sensors are sampled, such as to increase or decrease an amount of power consumed by the control circuitry.

Reduced Pressure Therapy Systems and Methods

FIG. 1 illustrates a negative pressure therapy system 100 that includes a TNP apparatus 11 and a wound 14. The TNP apparatus 11 can be used to treat the wound 14. The TNP apparatus 11 can include control circuitry 12A, memory 12B, a negative pressure source 12C, a user interface 12D, a power source 12E, a first pressure sensor 12F, a second pressure sensor 12G, and a skin detector 12H that are configured to electrically communicate with one another. In addition, the TNP apparatus 11 can include a wound dressing 13. The power source 12E can provide power to one or more components of the TNP apparatus 11.

One or more of the control circuitry 12A, memory device 12B, negative pressure source 12C, user interface 12D, power source 12E, first pressure sensor 12F, second pressure sensor 12G, and skin detector 12H can be integral with, incorporated as part of, attached to, or disposed in the wound dressing 13. The TNP apparatus 11 can accordingly be considered to have its control electronics and pump onboard the wound dressing 13 rather than separate from the wound dressing 13.

The control circuitry 12A can include one or more controllers (for example, a microcontroller or microprocessor), activation circuits, boost converters, current limiters, feedback conditioning circuits, and H-bridge inverters. The one or more controllers can control the operations of one or more other components of the TNP apparatus 11 according at least to instructions stored in the memory device 12B. The one or more controllers can, for instance, control operations of the negative pressure source 12C (for example, a pump) via a signal input (for example, a pulse width modulation (PWM) of the signal) to the one or more H-bridge inverters, which in turn drive power from the power source 12E to the negative pressure source 12C.

The negative pressure source 12C can include a pump, such as a rotary diaphragm pump or other diaphragm pump, a piezoelectric pump, a peristaltic pump, a piston pump, a rotary vane pump, a liquid ring pump, a scroll pump, a pump operated by a piezoelectric transducer, a voice coil pump, or any other suitable pump or micropump or any combinations of the foregoing. The pump can include an actuator driven by a source of energy, such as electrical energy, mechanical energy, and the like. For example, the actuator can be an electric motor, a piezoelectric transducer, a voice coil actuator, an electroactive polymer, a shape-memory alloy, a comb drive, a hydraulic motor, a pneumatic actuator, a screw jack, a servomechanism, a solenoid actuator, a stepper motor, a plunger, a combustion engine, and the like.

The user interface 12D can include one or more elements that receive user inputs or provide user outputs to a patient or caregiver. The one or more elements that receive user inputs can include buttons, switches, dials, touch screens, or the like, and the one or more elements that provide user outputs can include activation of a light emitting diode (LED) or one or more pixels of the display or activation of a speaker or the like. In one example, the user interface 12D can include a switch to receive user inputs (for instance, a negative pressure activation or deactivation input) and two LEDs to indicate an operating status (for example, functioning normally, under fault condition, or awaiting user input) of the TNP apparatus 11.

The first pressure sensor 12F can be used to monitor pressure underneath the wound dressing 13, such as pressure in a fluid flow path connecting the negative pressure source 12C and the wound 14, pressure at the wound 14, or pressure in the negative pressure source 12C. The second pressure sensor 12G can be used to monitor pressure external to the wound dressing 13. The pressure external to the wound dressing can be atmospheric pressure; however, the atmospheric pressure can vary depending on, for instance, an altitude of use or pressurized environment in which the TNP apparatus 11 may be used.

The control circuitry 12A can control the supply of negative pressure by the negative pressure source 12C according at least to a comparison between the pressure monitored by the first pressure sensor 12F and the pressure monitored by the second pressure sensor 12G. The control circuitry 12A can vary the sampling rate at which pressures monitored by the first and second pressure sensors 12F and 12G are sampled, such as based at least on an amount of energy stored in the power source 12E or whether the negative pressure source 12C is supplying negative pressure. The sampling rate can be varied, for instance, to increase an amount of power consumed (that is, by increasing the sampling rate) or decrease an amount of power consumed (that is, by decreasing the sampling rate) by the control circuitry 12A. A controller of the control circuitry 12A can enter a sleep mode, which may be a mode during which the pressure monitored by the first and second pressure sensors 12F and 12G is not sampled, and the controller can vary the sampling rate by entering the sleep mode. The sleep mode may be a mode from which the controller can be awoken via a hardware or software interrupt.

The skin detector 12H can be used to determine if the wound dressing 13 has been placed over the wound 14. For example, the skin detector 12H can be a part of the TNP apparatus 11 that makes contact with skin of a patient when the TNP apparatus 11 is placed on a patient to provide therapy, and the skin detector 12H can detect when the skin detector 12H is in contact with skin of a patient. The detection by the skin detector 12H can thus confirm whether the wound dressing 13 is coupled to skin of the patient next to the wound 14. The skin detector 12H can include one or more of a capacitive sensor, an impedance sensor, an optical sensor, a piezoresistive sensor, a piezoelectric sensor, an elastoresistive sensor, and an electrochemical sensor. The skin detector 12H can indicate detection of skin when a property (for instance, a resistance, capacitance, or color) monitored by the skin detector 12H varies in a way that indicates contact with skin rather than absence of contact with skin.

When skin is detected, this may indicate that activation of the TNP apparatus 11 is intentional rather than unintentional and can thus be used to prevent unintentional activation of the TNP apparatus 11 or an end-of-life timer of the TNP apparatus 11, such as during transportation or manufacture of the TNP apparatus 11. In one example, if the skin detector 12H indicates to the control circuitry 12A that skin is detected (for instance, in some cases, for a period of time like 0.1, 0.5, 1, 2, or 5 seconds), the control circuitry 12A can activate the negative pressure source 12C to supply negative pressure and activate an end-of-life timer in response to receiving an activation input via the user interface 12D. If the skin detector 12H, on the other hand, indicates to the control circuitry 12A that skin is not detected (for instance, in some cases, for a period of time like 0.1, 0.5, 1, 2, or 5 seconds), the control circuitry 12A may not activate the negative pressure source 12C to supply negative pressure or activate an end-of-life timer in response to receiving an activation input via the user interface 12D. In one example, an end-of-life timer can be a timer maintained by the control circuitry 12A that, while running, denotes that one or more functions of the TNP apparatus 11 (such as providing of negative pressure with the negative pressure source 12C or processing user inputs to the user interface 12D) is enabled. Upon expiration of the end-of-life timer (such as 1, 5, or 20 days after activation of the timer), the control circuitry 12A can disable the one or more functions of the TNP apparatus 11.

The wound dressing 13 can include a wound contact layer, a spacer layer, and an absorbent layer. The wound contact layer can be in contact with the wound 14. The wound contact layer can include an adhesive on the patient facing side for securing the dressing to the skin surrounding the wound 14 or on the top side for securing the wound contact layer to a cover layer or other layer of the wound dressing 13. In operation, the wound contact layer can provide unidirectional flow so as to facilitate removal of exudate from the wound while blocking or substantially preventing exudate from returning to the wound 14. The spacer layer can assist in distributing negative pressure over the wound site and facilitating transport of wound exudate and fluids into the wound dressing 13. Further, the absorbent layer can absorb and retain exudate aspirated from the wound 14.

The control circuitry 12A can cause the power source 12E to supply a greater amount of power upon expiration of an end-of-life timer to increase the rate at which the energy stored in the power supply 12E is exhausted. This may advantageously, in certain embodiments, make the TNP apparatus 11 safer to handle and dispose of after expiration of the end-of-life timer. In one example, the control circuitry 12A can close some or all of the switches of an H-bridge inverter to cause the H-bridge inverter to consume a greater amount of power.

The control circuitry 12A can, in some instances, prevent supply of negative pressure with the negative pressure source 12C. For example, the control circuitry 12A can prevent supply of negative pressure by deactivating operation of the negative pressure source, opening a vent positioned in the fluid flow path, and closing a valve positioned in the fluid flow path. In some implementations, the control circuitry 12A can prevent supply of negative pressure by the negative pressure source 12C in response determining that the skin detector 12H does not detect skin of the patient.

The control circuitry 12A can monitor a duty cycle of the negative pressure source 12C (for example, the duty cycle of the actuator of the negative pressure source). As is used herein, the "duty cycle" can reflect the amount of time the negative pressure source 12C is active or running over a period of time. In other words, the duty cycle can reflect time that the negative pressure source 12C is in an active state as a fraction of total time under consideration. Duty cycle measurements can reflect a level of activity of the negative pressure source 12C. For example, the duty cycle can indicate that the negative pressure source 12C is operating normally, working hard, working extremely hard, etc. Moreover, the duty cycle measurements, such as periodic duty cycle measurements, can reflect various operating conditions, such as presence or severity of leaks, rate of flow of fluid (for instance, air, liquid, or solid exudate, etc.) aspirated from a wound, or the like. Based on the duty cycle measurements, such as by comparing the measured duty cycle with a set of thresholds (for instance, determined in calibration), the controller can execute or be programmed to execute algorithms or logic that control the operation of the system. For example, duty cycle measurements can indicate presence of a high leak, and the control circuitry 12A can be programmed to indicate this condition to a user (for instance, patient, caregiver, or physician) or temporarily suspend or pause operation of the source of negative pressure in order to conserve power.

When the TNP apparatus 11 may be used to treat the wound 14, the wound dressing 13 can create a substantially sealed or closed space around the wound 13 and under the wound dressing 13, and the first pressure sensor 12F can periodically or continuously measure or monitor a level of pressure in this space. The control circuitry 12A can control the level of pressure in the space between a first negative pressure set point limit and at least a second negative pressure set point limit. In some instances, the first set point limit can be approximately −70 mmHg, or from approximately −60 mmHg or less to approximately −80 mmHg or more. In some instances, the second set point limit can be approximately −90 mmHg, or from approximately −80 mmHg or less to approximately −100 mmHg or more.

Figure 2A:
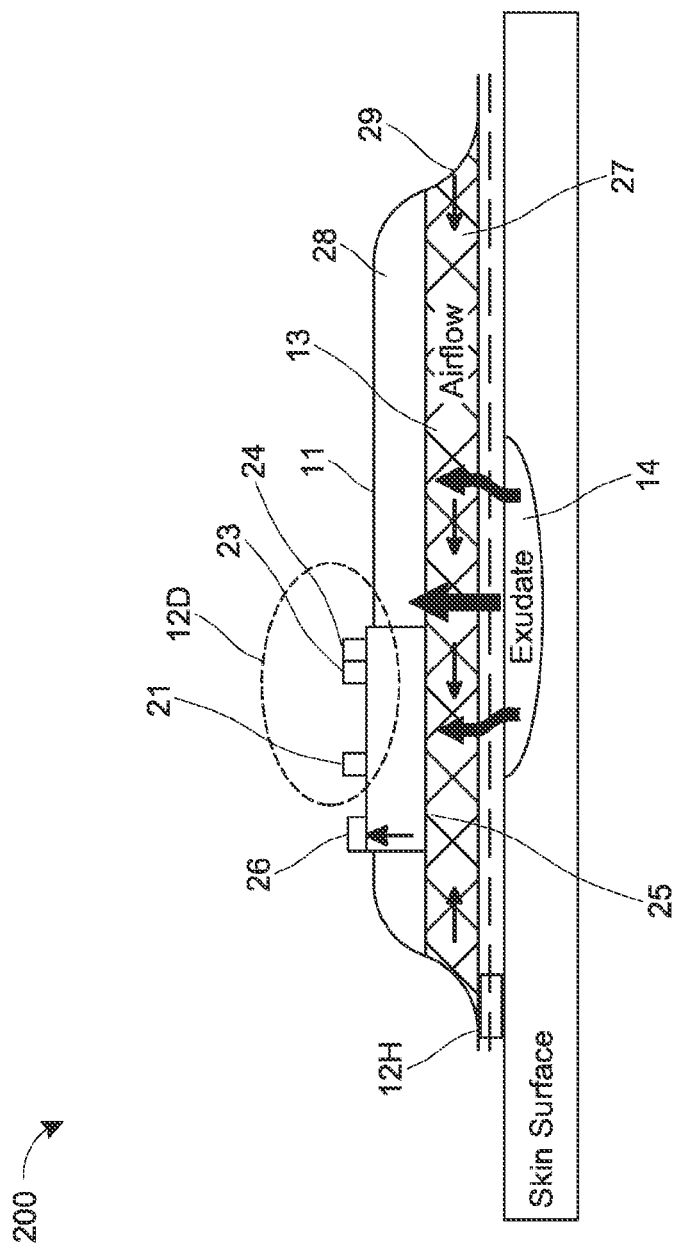
FIGS. 2A and 2B respectively illustrate a side view and top view of a negative pressure therapy system according to some embodiments, such as the negative pressure therapy system of FIG. 1.
Figure 2B:
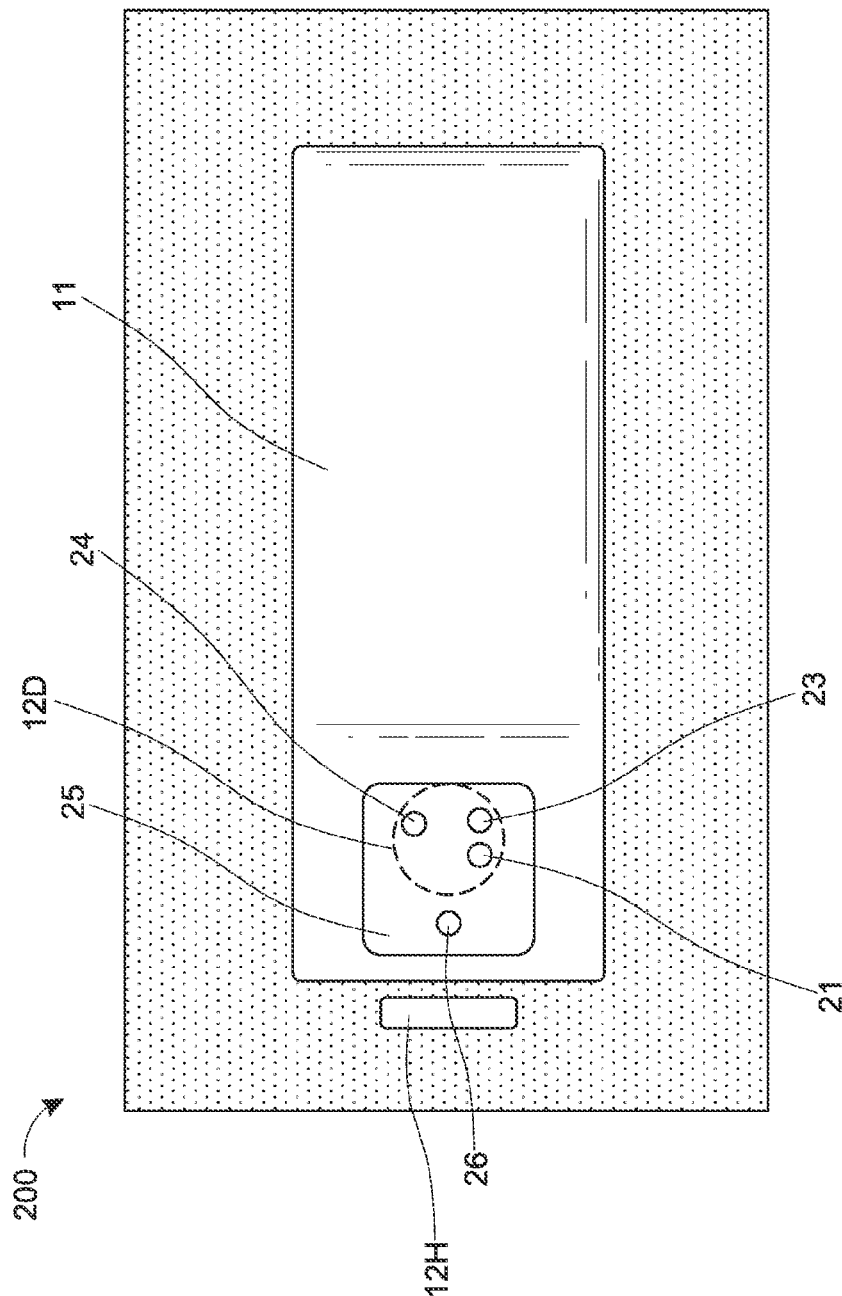

FIG. 2A illustrates a side view of a negative pressure therapy system 200, and FIG. 2B illustrates a top view of the negative pressure therapy system 200. The negative pressure therapy system 200 can be an example implementation of the negative pressure therapy system 100.

In the negative pressure therapy system 200, the wound dressing 13 of the TNP apparatus 11 is shown as attached to the wound 14. Arrows depict the flow of air through the wound dressing 13 and wound exudate from the wound 14. The TNP apparatus 11 can include an air exhaust 26 and a component area 25, such as a components housing or storage area for components of the TNP apparatus 11 like one or more of the control circuitry 12A, memory device 12B, negative pressure source 12C, user interface 12D, power source 12E, first pressure sensor 12F, and second pressure sensor 12G. The skin detector 12H can be positioned near a skin surface by the wound 14 and be electrically coupled to the control circuitry 12A to indicate whether skin is detected.

The user interface 12D of the negative pressure therapy system 200 can include a switch 21 (such as a dome switch), a first indicator 23 (such as a first LED), and a second indicator 24 (such as a second LED). The switch 21 can receive a negative pressure activation or deactivation user input (for example, such as receiving the activation or deactivation user input in response to depression of the switch 21 for a period of time, like from between 0.5 seconds and 5 seconds). The first indicator 23 and the second indicator 24 can indicate an operating status like functioning normally, under fault condition, or awaiting user input. In some implementations, the switch 21 can couple to a power supply connection of the negative pressure source 12C or the control circuitry 12A (such as a controller) or an enable signal of the negative pressure source 12C or the control circuitry 12A to activate or deactivate supply of negative pressure or disable supply of negative pressure.

Component parts of the wound dressing 13 of the negative pressure therapy system 200 are illustrated to include an airlock layer 27, an absorbing layer 28, and a contact layer 29. The airlock layer 27 can enable air flow. The absorbing layer 28 can absorb wound exudate. The contact layer 29 can be soft and include silicon and be used to couple the TNP apparatus 11 to the patient.

Figure 3:
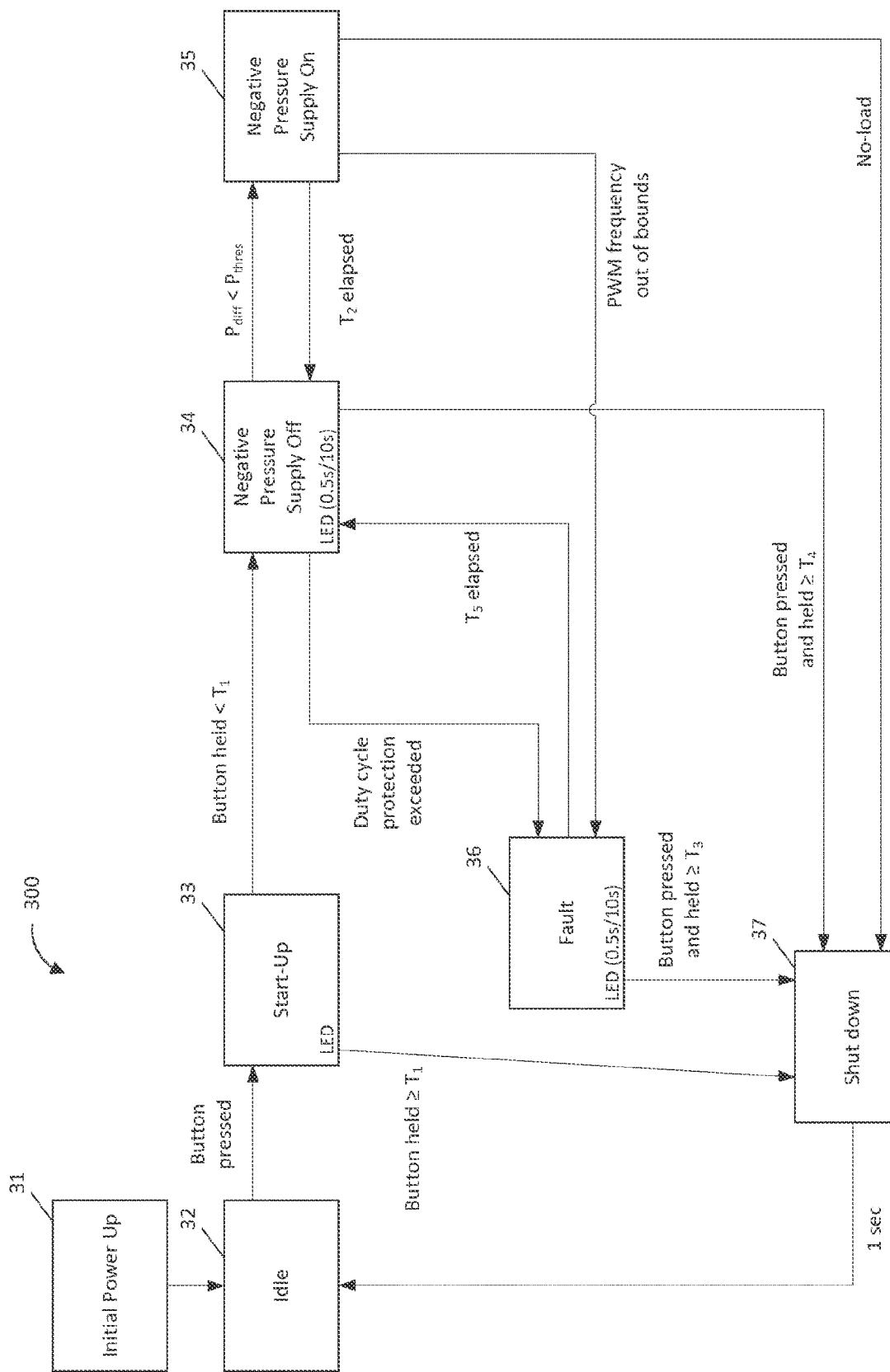
FIG. 3 illustrates a control state diagram usable to control operation of negative pressure therapy system according to some embodiments.

FIG. 3 illustrates a control state diagram 300 usable to control operation of a negative pressure therapy apparatus, such as the TNP apparatus 11. For convenience, the control state diagram 300 is described in the context of the TNP apparatus 11, but may instead be implemented in other systems described herein or by other computing systems not shown.

At state 31, the control circuitry 12A can power up. This can occur, for example, in response to the power source 12E being electrically coupled to the control circuitry 12A, such as by a user removing a tab that was electrically isolating the power source 12E and a controller of the control circuitry 12A so that the power source 12E and the controller are electrically coupled. At state 32, the control circuitry 12A can remain in an idle state, which can be a low power state where the controller consumes minimal power and draws minimal current (such as around 10, 30, 50, or 100 nA). When the switch 21 of the user interface 12D is pressed, the control state diagram 300 can transition to state 33, and the control circuitry 12A can initiate start-up. When the switch 21 is held less than a period of time $T_1$ (such as 0.5, 1, 2, 3, or 5 seconds), the control circuitry 12A may enter a negative pressure supply operation phase that includes states 34 and 35. When the switch 21 is held for the period of time $T_1$ or longer, the control state diagram 300 can transition to state 37, and the control circuitry 12A can initiate shut down and return to state 32.

Once in the negative pressure supply operation phase that includes states 34 and 35, the control circuitry 12A can attempt to deliver a desired level of negative pressure to the wound dressing 13 and control the supply of negative pressure with the negative pressure source 12C based at least on a magnitude of a pressure difference $P_{diff}$ between the pressure measured by the first pressure sensor 12F and the second pressure sensor 12G. For instance, at state 35, the control circuitry 12A can cause the negative pressure source 12C to supply negative pressure if $P_{diff}$ was be less than $P_{thres}$, such as 50, 70, 90, 93, 100, or 120 mBar. The control circuitry 12A can, for example, cause the negative pressure source 12C to supply negative pressure for a period of time $T_2$ (such as 0.05, 0.1, 0.25, 0.5, 1, or 2 seconds) and then at state 34 stop the supply of negative pressure and again determine if $P_{diff}$ may be less than $P_{thres}$.

The control state diagram 300 can transition from states 34 and 35 to state 36, which can be indicative of a fault condition, when one or more operating parameters indicate that the negative pressure source 12C is operating too quickly or slowly or not operating as instructed. For example, the fault condition can be determined based on a level of activity of the negative pressure source 12C satisfying a threshold. In one implementation, duty cycle or PWM information can be monitored by the TNP apparatus 11 and compared to one or more thresholds (for instance, indicating whether a duty cycle protection may be exceeded or a PWM frequency may be out of bounds).

The control state diagram 300 can transition from state 36 to state 37 when the switch 21 is pressed and held for a period of time $T_3$ (such as 0.5, 1, 2, 3, or 5 seconds) or longer. The control state diagram 300 can transition from state 34 to state 37 when the switch 21 is pressed and held for a period of time $T_4$ (such as 0.5, 1, 2, 3, or 5 seconds) or longer. The control state diagram 300 can transition from state 35 to state 37 when no load may be detected (for example, detecting a condition where a connection issue exists between the control circuitry 12A and the negative pressure source 12C, such as by detecting if a voltage of the power source 12E drops below a threshold like 5 V). The control state diagram 300 can transition from state 36 to state 34 when a period of time $T_5$ (such as 5, 10, 15, 20, 30, or 60 minutes) elapses without the switch 21 being pressed and held for the period of time $T_2$ or longer. One or more of the periods of time $T_1$, $T_3$, and $T_4$ can be the same or different from one another in some instances.

In some implementations, the first indicator 23 and the second indicator 24 can indicate which of the states 31-37 that the TNP apparatus 11 may be in via, for example, one or more of (i) activation or deactivation of one or both of the first indicator 23 and the second indicator 24 for period(s) of time or (ii) changing a color of the first indicator 23 or the second indicator 24.

Figure 4:
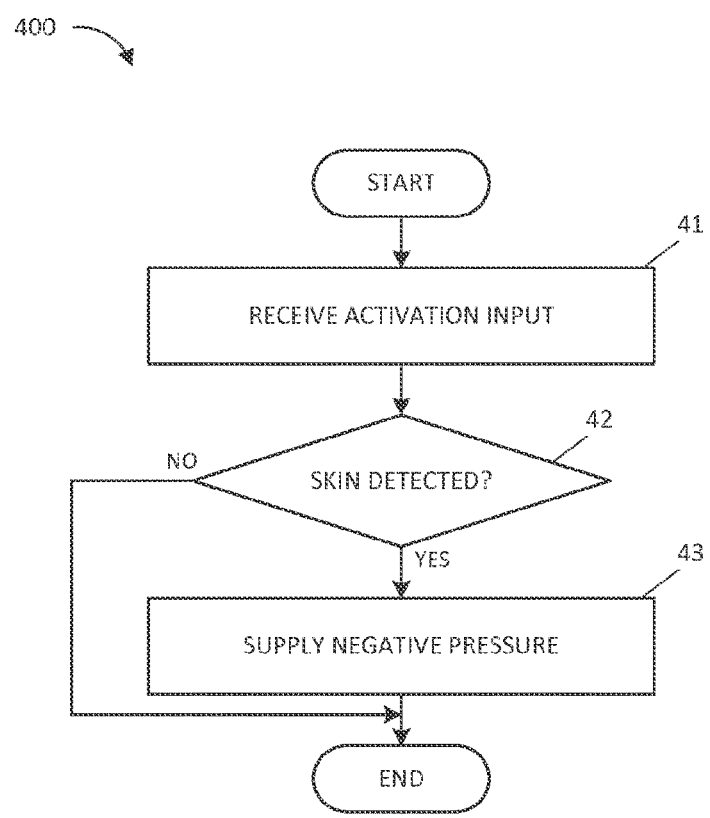
FIG. 4 illustrates a therapy initiation process performable by a negative pressure therapy system according to some embodiments.

FIG. 4 illustrates a therapy initiation process 400 performable by an apparatus, such as the TNP apparatus 11. For convenience, the therapy initiation process 400 is described in the context of the TNP apparatus 11, but may instead be implemented in other systems described herein or by other computing systems not shown. The therapy initiation process 400 can be performed, in some instances, by the control circuitry 12A of the TNP apparatus 11.

At block 41, the therapy initiation process 400 can receive an activation input. For example, the control circuitry 12A can receive an activation input via the user interface 12D. The activation input can be an input to the user interface 12D indicating to initiate supply of negative pressure with the negative pressure source 12C.

At block 42, the therapy initiation process 400 can determine if skin is detected. For example, the control circuitry 12A can determine if skin is detected by the skin detector 12H.

In response to determining that skin is detected, the therapy initiation process 400 can move to block 43 and begin supply of negative pressure. For example, the control circuitry 12A can initiate the supply of negative pressure to the wound dressing 13. Moreover, in some implementations, the control circuitry 12A can start an end-of-life timer in response to determining that skin is detected and beginning supply of negative pressure for the first time. The end-of-life timer can enable the TNP apparatus 11 to treat a single wound and then deactivate (for example, permanently) upon expiration of the end-of-life timer so that the TNP apparatus 11 is not usable to treat another wound.

On the other hand, in response to determining that skin is not detected, the therapy initiation process 400 can end, and the control circuitry 12A, for instance, may not initiate the supply of negative pressure.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract, and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:
    a wound dressing configured to be placed over a wound of a patient;
    a negative pressure source configured to provide negative pressure to the wound via a fluid flow path connecting the negative pressure source to the wound dressing;
    a user interface configured to receive an activation input;
    a first sensor integrated with the wound dressing, the first sensor configured to detect whether the wound dressing is positioned over the wound; and a control circuitry electrically coupled to the user interface and the first sensor, the control circuitry programmed to:
cause supply of negative pressure with the negative pressure source in response to receipt of the activation input by the user interface and a determination that the first sensor detects that the wound dressing is positioned over the wound, and
prevent supply of negative pressure with the negative pressure source in response to a determination that the first sensor does not detect that the wound dressing is positioned over the wound.

2. The apparatus of claim 1, wherein the control circuitry is further programmed to:
start a timer in response to receipt of the activation input by the user interface and the determination that the first sensor detects that the wound dressing is positioned over the wound; and
prevent supply of negative pressure with the negative pressure source in response to expiration of the timer.

3. The apparatus of claim 2, wherein the control circuitry is further programmed to not start the timer in response to the determination that the first sensor does not detect that the wound dressing is positioned over the wound.

4. The apparatus of claim 2, wherein the timer expires after between 5 days and 20 days.

5. The apparatus of claim 2, further comprising a power source configured to supply power to one or more of the negative pressure source or the control circuitry, the control circuitry being further programmed to increase an amount of power supplied by the power source in response to expiration of the timer.

6. The apparatus of claim 1, wherein the control circuitry is programmed to prevent supply of negative pressure with the negative pressure source by one or more of: deactivation of operation of the negative pressure source, opening of a vent positioned in the fluid flow path, or closing of a valve positioned in the fluid flow path.

7. The apparatus of claim 1, wherein the control circuitry is programmed to:
cause supply of negative pressure with the negative pressure source in response to receipt of the activation input by the user interface and the determination that the first sensor detects that the wound dressing is positioned over the wound for a period of time, and
prevent supply of negative pressure with the negative pressure source in response to the determination that the first sensor detects that the wound dressing is positioned over the wound for less than the period of time.

8. The apparatus of claim 1, wherein the first sensor comprises one or more of a capacitive sensor, an impedance sensor, an optical sensor, a piezoresistive sensor, a piezoelectric sensor, an elastoresistive sensor, or an electrochemical sensor.

9. The apparatus of claim 1, further comprising:
a second sensor configured to monitor pressure in the fluid flow path, and
a third sensor configured to monitor pressure outside the wound dressing,
wherein the control circuitry is further programmed to control supply of negative pressure with the negative pressure source according at least to a comparison of the pressure monitored by the second sensor and the pressure monitored by the third sensor.

10. The apparatus of claim 9, wherein the control circuitry is further programmed to:
determine a magnitude of a difference between the pressure monitored by the second sensor and the pressure monitored by the third sensor;
prevent supply of negative pressure with the negative pressure source in response to a determination that the magnitude satisfies a deactivation threshold; and
cause supply of negative pressure with the negative pressure source in response to a determination that the magnitude satisfies an activation threshold, the deactivation threshold being different from the activation threshold.

11. The apparatus of claim 9, wherein the control circuitry is further programmed to vary a sampling rate at which the pressure monitored by the second sensor and the pressure monitored by the third sensor are sampled.

12. The apparatus of claim 9, wherein the control circuitry is further programmed to enter a sleep mode in which the control circuitry does not sample the pressure monitored by the second sensor and the pressure monitored by the third sensor until the control circuitry leaves the sleep mode.

13. The apparatus of claim 1, wherein the control circuitry is programmed to enter a sleep mode in response to the determination that the first sensor does not detect that the wound dressing is positioned over the wound.

14. The apparatus of claim 1, wherein the control circuitry is programmed to enter a sleep mode while the negative pressure source supplies negative pressure.

15. A method of operating a negative pressure wound therapy apparatus, the method comprising:
receiving an activation input with a user interface;
at a first time, determining that a first sensor detects that a wound dressing is positioned over a wound;
in response to receiving the activation input and determining that the first sensor detects that the wound dressing is positioned over the wound, supplying negative pressure with a negative pressure source to the wound via a fluid flow path connecting the negative pressure source to the wound dressing;
at a second time, determining that the first sensor does not detect that the wound dressing is positioned over a wound; and
in response to determining that the first sensor does not detect that the wound dressing is positioned over the wound, preventing supply of negative pressure with the negative pressure source to the wound,
wherein the method is performed under control of a control circuitry of the negative pressure wound therapy apparatus.

16. The method of claim 15, further comprising:
starting a timer in response to receiving the activation input with the user interface and determining that the first sensor detects that the wound dressing is positioned over the wound; and
preventing supply of negative pressure with the negative pressure source to the wound in response to expiration of the timer.

17. The method of claim 15, wherein the activation input is indicative of an element of the user interface being depressed for a period of time, the period of time being between 0.5 seconds and 5 seconds.

18. The method of claim 15, further comprising determining whether the first sensor detects that the wound dressing in response to receiving the activation input with the user interface.

19. The method of claim 15, wherein said supplying negative pressure with the negative pressure source is controlled according at least to a comparison of a pressure monitored by a second sensor and a pressure monitored by a third sensor, the second sensor monitoring the pressure in the fluid flow path, and the third sensor monitoring the pressure outside the wound dressing.

20. The method of claim 15, further comprising:
  sampling a pressure monitored by a second sensor and a pressure monitored by a third sensor, the second sensor monitoring the pressure in the fluid flow path, and the third sensor monitoring the pressure outside the wound dressing; and
  varying a sampling rate at which the pressure monitored by the second sensor and the pressure monitored by the third sensor are sampled according to one or more of: (i) an amount of energy stored in a power source used to power the negative pressure source or the control circuitry or (ii) whether the negative pressure source is supplying negative pressure.

* * * * *